(12) United States Patent
Hilfrich

(10) Patent No.: US 10,852,303 B2
(45) Date of Patent: Dec. 1, 2020

US010852303B2

(54) SEROLOGIC TEST FOR THERAPY CONTROL OF HPV16 POSITIVE CARCINOMA

(71) Applicant: Abviris Deutschland GmbH, Ahrensburg (DE)

(72) Inventor: Ralf Hilfrich, Hünfelden (DE)

(73) Assignee: ABVIRIS DEUTSCHLAND GMBH, Ahrensburg (DE)

(*) Notice: Subject to any disclaimer, the term of this patent is extended or adjusted under 35 U.S.C. 154(b) by 0 days.

(21) Appl. No.: 16/090,159

(22) PCT Filed: Dec. 13, 2017

(86) PCT No.: PCT/EP2017/082506
§ 371 (c)(1),
(2) Date: Sep. 28, 2018

(87) PCT Pub. No.: WO2018/108957
PCT Pub. Date: Jun. 21, 2018

(65) Prior Publication Data
US 2019/0113516 A1    Apr. 18, 2019

(30) Foreign Application Priority Data

Dec. 13, 2016  (DE) .................. 10 2016 124 171

(51) Int. Cl.
| | | |
|---|---|---|
| *G01N 33/00* | (2006.01) | |
| *G01N 33/577* | (2006.01) | |
| *G01N 33/574* | (2006.01) | |
| *C12N 7/00* | (2006.01) | |
| *C07K 16/08* | (2006.01) | |
| *C12N 5/16* | (2006.01) | |
| *C12N 15/85* | (2006.01) | |
| *G01N 33/569* | (2006.01) | |

(52) U.S. Cl.
CPC ..... *G01N 33/57484* (2013.01); *C07K 16/084* (2013.01); *C12N 5/16* (2013.01); *C12N 7/00* (2013.01); *C12N 15/85* (2013.01); *G01N 33/57407* (2013.01); *C12N 2710/20022* (2013.01); *C12N 2710/20023* (2013.01); *G01N 33/56983* (2013.01); *G01N 2333/025* (2013.01); *G01N 2800/52* (2013.01)

(58) Field of Classification Search
None
See application file for complete search history.

(56) References Cited

U.S. PATENT DOCUMENTS

2013/0244228 A1* 9/2013 Hilfrich ............... G01N 33/558
435/5

OTHER PUBLICATIONS

De Gruijl et al. Immunoglobulin G Responses Against Human Papillomavirus Type 16 Virus-Like Particles in a Prospective Non-intervention Cohort Study of Women With Cervical Intraepithelial Neoplasia. J Natl Cancer Inst 1997;89:630-8.*
Skiba et al. Prognostic Significance of Serum Antibodies to HPV-16 L1 Virus-like Particles in Patients with Invasive Cervical Cancer. Anticancer Research 26: 4921-4926 (2006).*
Heim et al. Antibodies to human papillomavirus 16 L1 virus-like particles as an independent prognostic marker in cervical cancer. Am J Obstet Gynecol 2002;186:705-11.*
Christensen et al., "Surface Conformational and Linear Epitopes on HPV-16 and HPV-18 L1 Virus-like Particles as Defined by Monoclonal Antibodies," *Virology* 223:174-184, 1996.
Ochi et al., "Do Neutralizing Antibody Responses Generated by Human Papillomavirus Infections Favor a Better Outcome of Low-Grade Cervical Lesions?" *Journal of Medical Virology* 84:1128-1134, 2012.
Volpers et al., "Assembly of the Major and the Minor Capsid Protein of Human Papillomavirus Type 33 into Virus-like Particles and Tubular Structures in Insect Cells," *Virology* 200:504-512, 1994.
De Gruijl et al., "Immunoglobulin G Responses Against Human Papillomavirus Type 16 Virus-Like Particles in a Prospective Non-intervention Cohort Study of Women With Cervical Intraepithelial Neoplasia," Journal of the National Cancer Institute, vol. 89, No. 9, May 7, 1997, 630-638.
Geijersstam et al., "Stability over Time of Serum Antibody Levels to Human Papillomavirus Type 16," The Journal of Infectious Diseases, 1998;177:1710-4.
Koslabova et al., "Markers of HPV infection and survival in patients with head and neck tumors," Int. J. Cancer: 133, 1832-1839 (2013).
Mehlhorn et al., "HPV 16-L1-specific Antibody Response Is Associated with Clinical Remission of High-risk HPV-positive Early Dysplastic Lesions," Anticancer Research 34: 5127-5132 (2014).
Shah et al., "Antibodies to Human Papillomavirus 16 and Subsequent in Situ or Invasive Cancer of the Cervix," Cancer Epidemiology, Biomarkers & Prevention, vol. 6, 233-237, Apr. 1997.
Wang et al., "A monoclonal antibody against intact human papillomavirus type 16 capsids blocks the serological reactivity of most human sera", Journal of General Virology (1997) 78, 2209-2215.
St Guily et al., "Human papillomavirus genotype distribution in tonsil cancers", Head & Neck Oncology 2011, 3:6, 5 pages.

* cited by examiner

*Primary Examiner* — Nianxiang Zou
(74) *Attorney, Agent, or Firm* — Seed Intellectual Property Law Group LLP

(57) ABSTRACT

A method for therapy control of HPV16 positive carcinoma, an antibody for use in the corresponding diagnostic method as well as a test for performing the method. In particular, a serologic method for monitoring the development of the amount of antibodies in samples, which were taken from a patient before and after the treatment of a HPV16 positive carcinoma over a predetermined period of time. In addition, an immunologic test in the form of a kit, with which the method can be performed.

13 Claims, 1 Drawing Sheet

SEROLOGIC TEST FOR THERAPY CONTROL OF HPV16 POSITIVE CARCINOMA

BACKGROUND

Technical Field

The present disclosure relates to a method for therapy control of HPV16 positive carcinoma, an antibody for use in the corresponding diagnostic method as well as a test for performing the method.

Description of the Related Art

Meanwhile, more than 100 types of human papilloma viruses (HPV) are known, which can infect the epithelial cells of the skin or of various mucosae. HPV infections are widely spread and different HPV types are attributed to different clinical pictures. HPV of type 1 and HPV of type 2 cause warts on the hands and feet, while HPV of type 6 and HPV of type 11 genital warts. In many cases, such an infection has no clinical symptoms, but it can also result in a tumor-like growth of the affected epithelial cells. Even though such tumors are mostly benign and, as mentioned above, only lead to the formation of warts, it has meanwhile been established that some HPVs can also cause malignant changes and therefore be responsible for the development of cancer, for example in the genital region but also in the mouth or throat.

Therapy method of choice for these malignant tumors is surgery, radiotherapy, chemotherapy, immunotherapy or a combination of these methods. In the context of therapy control after treatment of HPV positive carcinoma, it is desirable to detect tumor cells remaining in the body but also a relapse or metastases early, so that treatment can be resumed, for example by chemotherapy or immunotherapy, before visible secondary tumors are formed.

Various publications deal with the determination of HPV specific antibodies in the serum of patients and the diagnostic and prognostic value of the obtained data with respect to the occurrence or reoccurrence of HPV positive carcinoma.

Particularly useful for deducing diagnostic or prognostic values are so-called tumor antigens, i.e., particular antigen structures, that are part of a tumor cell and specific for it, and which are recognized by the immune system and can cause an immune response. The so-called tumor antigens HPV E6 and HPV E7 are only suitable to a limited extent, however, because these protein antigens occur in all HPV types, are largely homologous and therefore do not allow a type specific assessment, not even when, for example, HPV16 specific E6 or E7 proteins are used for serologic detection. This type specific detection of the serologic response is necessary, however, to determine the reaction of the immune system to the HPV type, which caused the tumor, and not, for example, the immune response to a benign wart on the foot, which would be considered a false-positive result and could have fatal consequences for the patient.

HPV are dsDNA viruses. The non-encapsulated virions consist of icosahedral capsids. L1 (late protein 1) determines amongst other things the capsid formation of the HPV and is primarily responsible for the immunogenicity of HPV types.

Af Geijerstam et al. describe in *Journal of Infectious Diseases*, 177, 1998, 1710-1714 a study, in which serum levels of HPV16 capsid specific antibodies in primiparous women were determined over a period of time until the second pregnancy. It can be inferred from this study, that the amount of HPV16 capsid specific antibodies in the serum remains stable over several years and the amount of antibodies correlates with the number of sexual partners, but not with a medical condition.

A further study deals with the question, whether HPV16 infections represent a risk factor for the later occurrence of cervix carcinoma (Shah et al., *Cancer Epidemiology, Biomarkers & Prevention*, 6, 1997, 233-237). The presence of a larger amount of HPV16 capsid antibodies in the serum is associated with a higher risk for the occurrence of cervix carcinoma. It was also found in the tests that the HPV16 capsid antibodies did not recede noticeably over a period of 7 to 13 years.

Koslabova et al. stated in *International Journal of Cancer*, 133, 2013, 1832-1839, that a long lasting seropositivity against HPV16 virus like particles (VLPs), i.e., capsids, is observed after the therapy of tumor patients. This means that a decrease of the amount of L1 specific antibodies after therapy does not appear suitable to control the success of the therapy. It is mentioned in the summary, that the titer of the antibodies, which are specific for the HPV16 capsid antigens, does not change during the observation period after treatment. L1 therefore does not represent a marker, which might be suitable for monitoring the development or even to detect a relapse.

A further problem as already mentioned above is the lack of type specificity of the conventional antibody tests. L1 or also the main capsid protein of HPV can be in monomeric or multimeric form. Five single L1 proteins associate to build so-called capsomers (or pentamers). 72 capsomers, as sub-units of the capsids, associate to form the capsid of the viruses, in which the genetic material is packed during naturally occurring infection. Differences in the nucleic acid sequence of 10% within the L1 gene are defined as a requirement in order to describe a new HPV type. This means, that even different HPV types may be identical in almost 90% of the L1 gene and protein. Besides the main capsid protein (L1), there is also the minor capsid protein L2. The L2 protein is also a highly conserved, i.e., in large parts identical protein. The L2 protein is therefore also not specific for particular HPV types.

Nevertheless, there can be parts in both proteins, which are specific for particular HPV types (see, e.g., Christensen). That means, that type-specific and non-type-specific (group-specific e.g., for high risk types or also genus-specific) epitopes (binding sites for antibodies) may occur next to each other.

As the antibodies of the patient sample are of polyclonal origin, i.e., directed against many different antigens or different parts of an antigen, type-specific and non-type-specific L1 antibodies cannot be distinguished when using monomeric L1 proteins in a "traditional" arrangement of an ELISA test with peroxidase or fluorescent labeled anti-IgG specific conjugates. Merely the presence of anti-L1 antibodies of the more than 100 different HPV is detected, even if the L1 protein is derived from HPV type 16. Because of the very high homology of the protein within the group of HPV, the seeming type specificity of the used L1 antigen is very misleading.

As a result, HPV serology is not suitable for therapy control of HPV16 positive carcinoma because it is accepted in the state of the art, that the amount of antibodies remains stable over years and does not necessarily decrease after therapy, so that this parameter is not suitable for a monitoring the condition. Furthermore, the different HPV types cannot be distinguished using conventional antibody tests.

BRIEF SUMMARY

Surprisingly, it was found out now, that for particular HPV16 L1 capsid specific antibodies, which bind to at least one conformational epitope of the HPV16 L1 capsid, which is not present in monomeric and/or denatured HPV16 L1 proteins, a decrease and a rebound of the amount of antibodies is observed. Thus, for the first time, not only a diagnostic determination of the ad hoc amount of HPV16 L1 capsid specific antibodies is possible but also the detection of a relapse.

When an HPV16 positive primary tumor is treated, within a few weeks (e.g., two weeks), normally in the context of a monitoring, a decrease of the amount of HPV16 specific L1 antibodies can be observed. The amount decreases steadily, but levels off at a ground line, so that a plateau is formed (FIG. 1). If HPV16 positive cells of the primary tumor remaining in the body start to grow again (relapse or metastasis), a quick increase of the amount of antibodies is observed (FIG. 2).

This change (rebound) of the amount of antibodies is already observed in the case of a microscopically small, for a clinician not visible secondary tumor, so that at the rebound therapy measures can be initiated much earlier than commonly done today and the chance of healing for the patient increases significantly.

Provided are methods for therapy control of HPV16 positive carcinoma, an antibody for use in the corresponding diagnostic method as well as a test for performing the method. In particular, a serologic method for monitoring the development of the amount of antibodies in samples, which were taken from a patient before and after the treatment of a HPV16 positive carcinoma over a predetermined period of time is provided. In addition, an immunologic test in the form of a kit, with which the method can be performed, is provided.

Provided is a serologic test, which allows a highly sensitive and type specific therapy control of HPV16 positive carcinoma and facilitates detection of a reoccurrence of the disease, such as a relapse or a metastasis, at an early stage.

Also provided is an in vitro method for therapy control after treatment of HPV16-positive carcinoma comprising the steps of (a) contacting a sample from a patient with an HPV16-positive carcinoma, said patient having been administered an anti-cancer therapy, with a plurality of antigens comprising a conformational epitope of HPV16 L1 capsid or capsomer, wherein said epitope is not present in monomeric and/or denatured HPV16 L1, under conditions at which antibodies present in the sample can bind to the antigens and (b) detecting the binding of antibodies in the sample bound to the antigen, wherein the binding of said antibodies bears a negative correlation with the success of anti-cancer therapy in the patient.

A sample may be taken from the patient before the treatment or at the time the anti-cancer therapy is initiated, to obtain a reference value of the amount of antibodies in the sample, to which later samples can be compared. Antibody levels as high as up to 50,000 ng/ml may be observed at this time in a patient.

In embodiments, the binding of antibodies in the sample bound to the antigen is detected by contacting the sample with labeled antibodies that specifically bind to the conformational epitope of the HPV16 L1 capsid or capsomer, for example with labeled antibodies obtained from the hybridoma cell line with the deposit number DSM ACC3306.

In further embodiments, the binding of said antibodies is compared with a reference level of binding, for example wherein the binding of said antibodies is compared with the binding of said antibodies in one or more samples taken from said patient at predetermined time intervals, wherein a decrease in said binding over a predetermined time indicates successful anti-cancer therapy and wherein an increase in said binding over time indicates a recurrence of the HPV16-positive carcinoma in said patient.

The labeled antibodies may be present in mobile form on a test strip and wherein complexes of antigen and labeled antibody are detected by binding to another antibody, for example wherein the other antibodies are also ones that are obtained from the hybridoma cell line with the deposit number DSM ACC3306.

In the described method, a patient identified as having a recurrence of the HPV16 positive carcinoma may be administered an anti-cancer therapy.

According to a preferred embodiment, the method for therapy control after treatment of HPV16 positive carcinoma comprises or consists of the following steps:

i) Mixing a sample of a patient with a plurality of antigens, wherein the antigens present HPV16 L1 capsid or capsomer structures, which have conformational epitopes not present in monomeric and/or denatured HPV16 L1, under conditions at which antibodies present in the sample can bind to the HPV16 L1 antigens, ii) Contacting the mixture of step i) with labeled antibodies, which specifically bind to the conformational epitopes of the HPV16 L1 capsid or capsomer structure presenting antigens, particularly with labeled antibodies, which are obtained from the hybridoma cell line with the deposit number DSM ACC3306, iii) Quantifying the labeled antibodies and/or the antibodies of the sample, which have bound to the HPV16-L1 capsid or capsomer structure presenting antigens, respectively, iv) Repeating steps i) to iii) one or more times with samples taken from the same patient in predetermined time intervals so that a trend of the amount of antibodies, that bind to the HPV16 L1 capsid or capsomer structure presenting antigens, in the patient is tracked based on the samples over a predetermined period of time, and v) Determining the amount of antibodies that bind to the HPV16 L1 capsid or capsomer structure presenting antigens in the samples to observe a decrease of the amount after successful therapy, and/or vi) Determining the amount of antibodies that bind to the HPV16 L1 capsid or capsomer structure presenting antigens in the samples to observe a reoccurrence of a HPV16-positive carcinoma, if the amount of antibodies that bind to the HPV16 L1 capsid or capsomer structure presenting antigens increases again in the sample within the predetermined period of time.

The method allows to quantify the amount of antibodies in the sample of the patient over a period of time and thus to track the development of the condition after therapy. For example, steps i) to iii) can be repeated every 1 to 4 weeks over a period of one to ten years.

In case of a successful therapy, the amount of antibodies found in the sample of the patient may decrease by over 50% within a couple of weeks compared to the amount of antibodies found before or at the beginning of the treatment.

In the method, antigens or virus like particles can be used, which present the HPV16 L1 capsid or capsomer structures, having conformational epitopes. For example, the conformational epitopes specifically bind antibodies, which are obtained from the hybridoma cell line with the deposit number DSM ACC3306.

As a sample, a body fluid is suitable, e.g., whole blood or derivatives of whole blood such as, e.g., serum or plasma, as well as capillary blood or whole blood from the finger pad of the patient. To perform the method, one drop (approx. 25 µL) is sufficient.

In step i), the sample of the patient can be incubated over a period of 1 to 15 minutes, for example, 3 to 10 minutes. Thus, specific interactions are ensured.

The therapy is in particular a primary therapy by surgery, radiotherapy, chemotherapy or immunotherapy or a combination of these methods.

Typically, in female patients 93% of HPV16-positive carcinoma are found in the anogenital area and only 7% in the mouth or throat, while in male patients about 80% are localized in the mouth or throat and only 20% in the anogenital area.

An HPV16 L1 capsid or capsomer structure is an aggregate or a multimer of the HPV16 L1 protein, which, by interaction of several L1 proteins, forms conformational epitopes on its surface, which are not present in L1 monomers or denatured proteins. In particular, virus like particles (VLPs) are used, which present the HPV16 L1 capsid or capsomer structures. Some VLPs may carry several of the conformational epitopes, i.e., specific binding sites.

A virus like particle (VLP) is a virus particle, which consists of viral capsids, but does not contain nucleic acids. The VLPs are therefore suitable to present the above mentioned conformational epitopes without being capable of replication.

The labeled antibodies are antibodies directed against the HPV16 L1, which specifically binds to the conformational epitopes of the HPV L1 capsid or capsomer structures and thus not to monomeric and/or dentatured HPV16 L1 proteins. A preferred antibody can be obtained from the hybridoma cell line, which was deposited under the Budapest Treaty at the Deutsche Sammlung für Mikroorganismen and Zellkulturen (DSMZ), Inhoffenstraße 7B, 38124 Braunschweig, Germany, on 14 Sep. 2016 by Abviris Deutschland GmbH, Ammersbeck, under the deposit number DSM ACC3306. For the labeling of the antibody, the skilled person is aware of suitable methods of the state of the art, which allow a quantification of the amount of bound and unbound antibodies. In embodiments, the antibody is labeled with gold particles.

For the detection, commercially available readers for test strips, e.g., EseQuant by QIAGEN may be used. The measurement can be performed photo-optically or by determining the conductivity. Alternatively, colored or radioactively-labeled particles (vesicles) can be used.

The method is absolutely specific for HPV type 16 and there is no cross-reaction with other antibodies. The reason for this is in particular, that the capsomer structures are present as L1 aggregates, whereby the conformational epitopes are presented on the surface.

When the L1 protein forms aggregates (synonyms are multimers, pentamers or also capsomers), structures (conformational epitopes binding sites for antibodies) are formed on the surface (the areas of the capsids that are oriented towards the outside) of these aggregates by interaction of several L1 proteins, which are specific for particular HPV types (i.e., type specific).

On the other hand, the highly homologous areas of the L1 protein are oriented such that they are not on the surface but in the inside. These areas are necessary for the integration of the viral genetic material. That means, that for the viruses or the non-infectious virus like particles (VLPs) used in testing, the above described areas, which strongly match within the family of the papilloma viruses, are hidden inside the particles. These areas are thus no longer accessible in VLPs for the group specific antibodies in the human samples, whereby it is ensured that exclusively type specific antibodies are detectable.

However, monomeric protein cannot be removed by 100% during VLP purification. Purified VLPs therefore always contain also capsomers. This means, that if these purified L1 proteins are directly immobilized on a carrier medium (e.g., on classic ELISA plates), both, type specific VLPs but also monomeric L1 protein and capsomers with non-type specific areas are available for testing.

This contamination of the type specific L1 VLPs with monomeric or dentatured protein results in the type specific antibodies in a mixture of antibodies, such as human samples, being no longer (reliably) identifiable because it cannot be determined whether the test result can be attributed to the type specific or the group specific binding sites.

The same is true for VLPs, which consist of the L1 and the L2 protein.

Using the approach of competition between the patient antibodies and the HPV16 specific L1 antibodies according to the disclosure, this contamination problem can be solved because the test system can exclusively measure HPV16 L1 specific antibodies, which compete with the antibody according to the disclosure.

It is therefore preferred that the antigens are not immobilized but are provided in a liquid phase, to which the patient sample is added.

This has major advantages or, respectively, the following background: By immobilization and the subsequent preservation (by drying loss of hydrate shell causes conformational changes of the protein) required for selling the ELISA plates, the antigens (VLPs) are changed, i.e., they lose their type specific epitopes and thus become useless for testing. When adding the patient sample to the VLP solution, the antibodies of the patient sample and the antigen come into close proximity. Thus, the kinetics of the binding reaction become significantly faster, which is extremely useful for a quick test. Furthermore, the analytic sensitivity is increased because all antibodies in the patient sample are "quickly" available for the testing.

When immobilized on a carrier material, e.g., a microtiter plate, on the other hand, only the antibodies in close proximity to the surface are available as reactants. The antibodies within the lumen of the reaction vessel will practically "never" reach the surface of the reaction vessel because they have to cross the distance of 1-2 mm to the surface exclusively by Brownian motion, which takes "a lot" of time.

Described is also a method as described above, wherein the patient sample is simultaneously mixed with the antigens and contacted with the labeled antibodies.

Advantageously, it is also possible to simultaneously mix the patient sample with the antigens and contact it with the antibodies. This way, a direct competition between the antibodies from the patient sample and the labeled antibodies for the binding sites is achieved, which due to the fast binding kinetics as described above leads to more accurate test results. Accordingly, the test method can be performed in one step.

Further described is a method as described above, wherein in step ii) the mixture runs across a test strip, on which the labeled antibodies are present in mobile form and wherein in step iii) complexes of antigen and labeled antibody are detected by binding to another antibody, wherein preferably the other antibodies are also ones that are obtained from the hybridoma cell line with the deposit number DSM ACC3306.

This embodiment allows to provide a quick test, in which in a reaction zone, a quickly readable test result line becomes visible.

The mixture of step i) is applied at an application area on the test strip and then runs, for example by using capillary forces, across a membrane, during which it comes into contact with the labeled antibodies on a stretch up to the reaction zone. The labeled antibodies are concentrated such that not all antigens or binding sited are filled up. In the reaction zone, further antibodies are immobilized, which are also specific for the antigens or binding sites described herein and bind the labeled antibody-antigen complexes, insofar as free binding sites are still available. Thus, the labeled antibody-antigen complexes are retained in the reaction zone, whereby a test line becomes visible. In case the antigens or binding sites, respectively, are already occupied by antibodies from the patient sample, due to the competitive approach, less antibody-antigen complexes are formed with the labeled antibodies and the test line is less intense or not visible at all, that is, in case all binding sites were already occupied by the antibodies from the patient sample at the time of application. The correct adjustment of the amount of antigens or binding sites, respectively, in step i) and labeled antibodies in step ii) is important in this context, so that a change in the amount of antibodies in the patient sample with respect to a previous measurement can be detected.

Described is a method of treating a patient that has previously been administered at least one anti-cancer therapy targeting an HPV16-positive carcinoma comprising (A) requesting a test providing results of an analysis to determine whether the patient has an increase in antibodies that bind to a conformational epitope of HPV16 L1 capsid or capsomer over a predetermined time period and (B) administering an additional anti-cancer therapy targeting HPV16-positive carcinoma if an increase in antibodies is detected in the patient.

Further described is an antibody, which specifically binds to conformational epitopes of HPV16-L1 capsid or capsomer structure presenting antigens, for example an antibody, which is obtained from the hybridoma cell line with the deposit number DSM ACC3306.

Also described is an antibody as described above for use in a diagnostic method, in particular in a method for determining the reoccurrence of a HPV16-positive carcinoma after treatment.

Moreover, described is an antigen, which presents HPV16 L1 capsid or capsomer structures or a virus like particle, which presents the HPV16 L1 capsid or capsomer structures.

Described is an antigen or a virus like particle, which presents HPV16 L1 capsid or capsomer structures having conformational epitopes that specifically bind an antibody obtained from the hybridoma cell line with the deposit number DSM ACC3306.

An antigen or a virus like particle as described above for use in a diagnostic method, in particular in a method for determining the reoccurrence of a HPV16-positive carcinoma after treatment is also described. Further described is a kit for determining an amount of antibodies in a sample of a patient comprising or consisting of:

I) a composition comprising antigens presenting conformational epitopes of HPV16 L1 capsid or capsomer structures, and II) a composition comprising labeled antibodies, which specifically bind to conformational epitopes of HPV16 L1 capsid or capsomer structure presenting antigens, wherein preferably the labelled antibodies are obtained from the hybridoma cell line with the deposit number DSM ACC3306.

The composition i) is preferably a composition, which comprises virus like particles, which present conformational epitopes of HPV16 L1 capsid or capsomer structures.

A kit can also comprise a test strip, which optionally is provided in a testing cassette, which has openings for applying the mixture of step i) as well as for observing a test line and preferably a control line. The test strip comprises on one end an application zone for the mixture of step i), a pad, on which the labeled antibodies are provided and which connects to the application zone, as well as a reaction zone, which connects on the other side of the pad when viewed from the application zone and preferably a control zone, further beyond the reaction zone. In the reaction zone, the further antibody is provided, which specifically binds the epitope described herein and by binding of the labeled antibody-antigen complexes makes the test line visible. Another independent antibody reaction in the control zone shows that the test proceeded correctly. The appearance of a line in the control zone confirms that the sample volume was sufficient and the test ran as intended.

DETAILED DESCRIPTION

Example 1

Screening for the Antibodies and Antigens

Figure 1:
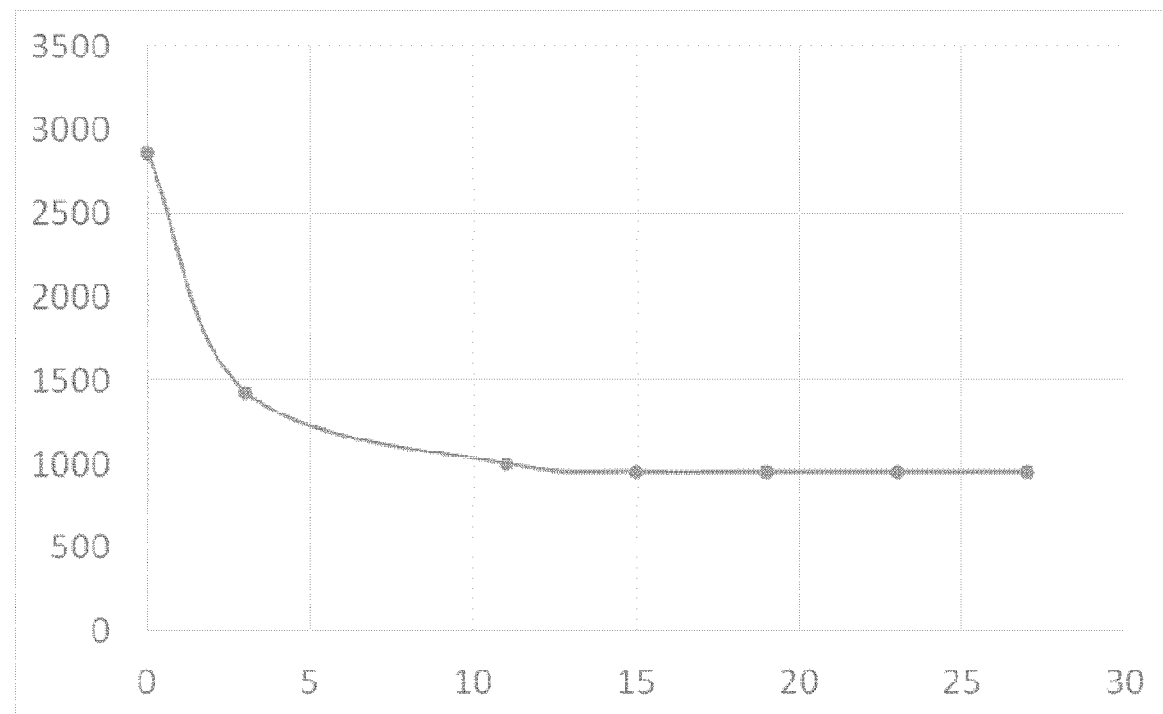
FIG. 1 shows the development of the amount of antibodies in the serum of a patient with a positive therapy course over 27 weeks after primary therapy of a HPV16 positive carcinoma. On the X axis, the weeks starting from 0 at the point in time of the primary therapy are shown, on the Y axis, the concentration of the antibody is shown in ng/ml.
Figure 2:
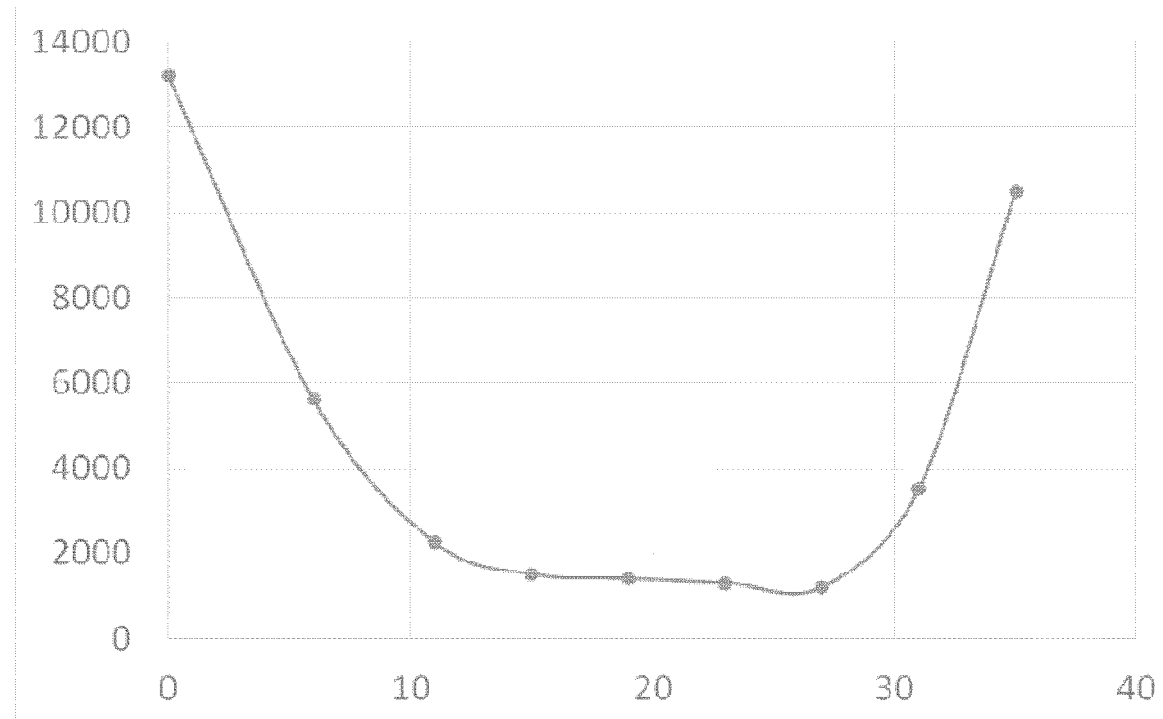
FIG. 2 shows the development of the amount of antibodies in the serum of a patient, in which after about 35 weeks after the primary therapy of a HPV16 positive carcinoma, a relapse occurred. Up to week 27, a continuous decrease of the amount of antibodies was observed. Beginning in week 31, the amount of antibodies increased again. The increase continued until week 35, at which time the clinical correlation was found. On the X axis, the weeks starting from 0 at the point in time of the primary therapy are shown, on the Y axis, the concentration of the antibody is shown in ng/ml.

Preparation of papillom virus like particles (VLPs): The L1 gene of HPV16 (GenBank: K02718.1) was amplified by PCR and cloned into the transfer vector pVL1392. The recombinant vectors were introduced in Sf9 cells together with BaculoGold DNA (Pharmingen) using calcium phosphate precipitation. Recombinant viruses were amplified and purified by plaque assay according to manufacturer's instructions.

Virus like particles (VLPs) were purified according to Volpers et al. (Volpers, C., P. Schirmacher, R. E. Streeck, and M. Sapp. 1994. Assembly of the major and the minor Kapsid protein of human papilloma virus type 33 into virus-like particles and tubular structures in insect cells. Virology 200:504-512).

Production, screening and cloning of the monoclonal antibodies. BALB/c mice were subcutaneously immunized with 20 μg of intact HPV16 VLPs dissolved in phosphate buffered salt solution (PBS), after these had been mixed with complete Freund's adjuvant. The immunization was repeated after one month and after three months.

Three days after the third immunization the spleen was taken out and a single cell suspension was produced. The spleen cells were fused with the mouse myeloma cell line X63Ag8.653 using polyethylene glycol 2500 (Boehringer Mannheim) and cultured in Iscoves modified Eagle Medium (IMDM) in the presence of 10% fetal calf serum in 96-well plates. Fused cells were selected with azaserine and hypoxanthine. After 6 to 8 days, the supernatant of the cells was tested for secretion of HPV16 L1 specific antibodies using ELISA. Denatured L1 protein, as well as VLPs of HPV-6, HPV-11, HPV-18, HPV-31, HPV-33 and HPV-39 served as controls to exclude unspecific reactivities.

Example 2

Observation of the Decrease of the Amount of Antibodies in a Patient after Successful Therapy Male Patient, age 53, with oncologic combination therapy (surgery/radio-chemotherapy) for a HPV16 positive tonsillar carcinoma. On the day before the therapy began, 5 ml blood were taken from the patient to obtain patient serum. Testing of the serum at the beginning of the therapy gave an antibody concentration of 13200 ng/ml.

Six weeks after the primary therapy, 5 ml blood were taken from the patient again to obtain serum. An antibody concentration of 5600 ng/ml was measured. This corresponds to a decrease of the antibody concentration of over 50% within 6 weeks.

With the decrease of the amount of antibodies, a successful therapy can be controlled because the tumor antigen HPV16 L1 forming tumor cells were successfully removed and the tumor antigen (HPV16 L1 protein) does not induce the immune system anymore to form HPV16 L1 specific antibodies.

The invention claimed is:

1. A method for continued treatment of HPV16-positive carcinoma in a patient, the method comprising:
   (a) contacting a sample from the patient with an HPV16-positive carcinoma, said patient having been administered an anti-cancer therapy, with a plurality of antigens comprising a conformational epitope of HPV16 L1 capsid or capsomer, wherein said epitope is not present in monomeric and/or denatured HPV16 L1, under conditions at which antibodies present in the sample can bind to the antigens;
   (b) detecting antibody levels in the sample that bind to the antigens;
   (c) comparing the antibody levels to a reference level of antibodies, wherein the reference level of antibodies is from a sample taken from the patient prior to the anti-cancer therapy, wherein a reduction in the antibody levels is indicative the anti-cancer therapy in the patient is working, and wherein an increase in the antibody levels is indicative the anti-cancer therapy in the patient is not working; and
   (d) administering an additional anti-cancer therapy targeting HPV16-positive carcinoma in the patient, wherein the patient has an increase in the antibody levels compared to the reference level of antibodies.

2. The method according to claim 1, wherein detecting antibody levels in the sample includes contacting the sample with labeled antibodies that specifically bind to the conformational epitope of the HPV16 L1 capsid or capsomer.

3. The method according to claim 2, wherein the labeled antibodies are present in mobile form on a test strip, and wherein complexes of the antigen and the labeled antibody are detected by binding to a subsequent antibody.

4. The method according to claim 1, wherein the patient is identified as having a recurrence of the HPV16 positive carcinoma.

5. A method for continued treatment of HPV16-positive carcinoma in a patient, the method comprising:
   i) mixing a sample of the patient with a plurality of antigens, said patient having been administered an anti-cancer therapy, wherein the antigens present HPV16 L1 capsid or capsomer structures, which have HPV16 L1 conformational epitopes not present in monomeric and/or denatured HPV16 L1, under conditions at which antibodies present in the sample can bind to the HPV16 L1 antigens,
   ii) contacting the mixture of step i) with labeled antibodies, which specifically bind to the conformational epitopes of the HPV16 L1 capsid or capsomer structure presenting antigens,
   iii) quantifying a level of the labeled antibodies and/or the antibodies of the sample, which have bound to the HPV16 L1 capsid or capsomer structure presenting antigens, respectively,
   iv) repeating steps i) to iii) one or more times with samples taken from the same patient in predetermined time intervals so that a trend of the level of antibodies that bind to the HPV16 L1 capsid or capsomer structure presenting antigens in the patient is tracked based on the samples over a predetermined period of time,
   v) determining the level of antibodies that bind to the HPV16 L1 capsid or capsomer structure presenting antigens in the samples,
   vi) comparing the level of antibodies determined in step v) with a reference level of antibodies, wherein the reference level of antibodies is from a sample taken from the patient prior to the anti-cancer therapy, wherein a decrease of the level of antibodies that bind over the predetermined period of time indicates the therapy is working, and wherein an increase in the level of antibodies that bind over the predetermined period of time indicates a reoccurrence of the HPV16-positive carcinoma, and
   vii) administering an additional anti-cancer therapy targeting HPV16-positive carcinoma in the patient, wherein the patient has an increase in the antibody levels compared to the reference level of antibodies.

6. The method according to claim 1, wherein the antigens are not immobilized but are provided in a liquid phase, to which the patient sample is added.

7. The method according to claim 2, wherein the patient sample is simultaneously contacted or mixed with the antigens and contacted with the labeled antibodies.

8. The method according to claim 5, wherein in step ii) the mixture runs across a test strip, on which the labeled antibodies are present in mobile form, and wherein in step iii) complexes of antigen and labeled antibody are detected by binding to another antibody.

9. The method according to claim 2, wherein the labeled antibodies are obtained from the hybridoma cell line with the deposit number DSM ACC3306.

10. The method according to claim 1, wherein the reference level of antibodies are a plurality of reference levels of antibodies taken from the patient at predetermined time intervals.

11. The method according to claim 3, wherein the subsequent antibody is one that is obtained from the hybridoma cell line with the deposit number DSM ACC3306.

12. The method according to claim 8, wherein the another antibody is obtained from the hybridoma cell line with the deposit number DSM ACC3306.

13. The method according to claim 5, wherein the labeled antibodies are obtained from the hybridoma cell line with the deposit number DSM ACC3306.

* * * * *